United States Patent
Atabey

(10) Patent No.: US 10,010,332 B2
(45) Date of Patent: Jul. 3, 2018

(54) CUTTING TOOL AND CORRESPONDING ASSEMBLY

(71) Applicant: Pratt & Whitney Canada Corp., Longueuil (CA)

(72) Inventor: Fuat Atabey, Brossard (CA)

(73) Assignee: PRATT & WHITNEY CANADA CORP., Longueuil, QC (CA)

( * ) Notice: Subject to any disclaimer, the term of this patent is extended or adjusted under 35 U.S.C. 154(b) by 541 days.

(21) Appl. No.: 14/167,302

(22) Filed: Jan. 29, 2014

(65) Prior Publication Data

US 2015/0209054 A1    Jul. 30, 2015

(51) Int. Cl.
  *A61B 17/16*    (2006.01)
  *B23C 5/00*     (2006.01)
  *B23C 5/10*     (2006.01)

(52) U.S. Cl.
  CPC .......... *A61B 17/1615* (2013.01); *B23C 5/003* (2013.01); *B23C 5/1009* (2013.01); *B23C 2210/086* (2013.01); *B23C 2210/088* (2013.01); *B23C 2210/486* (2013.01); *B23C 2215/04* (2013.01); *B23C 2220/605* (2013.01); *B23C 2265/08* (2013.01)

(58) Field of Classification Search
  CPC ... A61B 17/1615; B23C 5/1009; B23C 5/003; B23C 2210/486
  See application file for complete search history.

(56) References Cited

U.S. PATENT DOCUMENTS

| | | | | |
|---|---|---|---|---|
| 2,855,657 A | * | 10/1958 | Erhardt | B23C 5/04 407/115 |
| 3,736,634 A | * | 6/1973 | Sonnie | B23C 5/10 407/54 |
| 4,721,421 A | * | 1/1988 | Klinger | B23C 5/10 407/116 |
| 5,160,232 A | | 11/1992 | Maier | |
| 5,562,370 A | | 10/1996 | Vogel et al. | |
| 5,772,365 A | | 6/1998 | Vogel et al. | |
| 6,164,876 A | * | 12/2000 | Cordovano | B23C 5/10 407/59 |
| 6,796,751 B2 | | 9/2004 | Flolo | |
| 8,226,334 B2 | | 7/2012 | Hanks et al. | |
| 8,277,152 B2 | | 10/2012 | Azegami | |

(Continued)

FOREIGN PATENT DOCUMENTS

WO    WO2009/066935    *    5/2009

*Primary Examiner* — David Bates
(74) *Attorney, Agent, or Firm* — Norton Rose Fulbright Canada LLP

(57) ABSTRACT

A one-piece cutting tool has a shank portion with a mounting end and a cutting end. The cutting end has a body portion and a substantially hemispherical portion. The cutting end further comprises a plurality of flutes, each flute helically extending adjacent to one another about the cutting end along a length from the body portion to the hemispherical portion. Each flute has a cutting edge divided into a first cutting edge section and a second cutting edge section, the first cutting edge section extending along the body portion and being substantially straight-edged or serrated, and the second cutting edge section extending along the hemispherical portion and being serrated along at least a part of the hemispherical portion. A cutting tool assembly is also provided.

16 Claims, 5 Drawing Sheets

(56) References Cited

U.S. PATENT DOCUMENTS

| | | | |
|---|---|---|---|
| 8,402,867 B2 | 3/2013 | Harif | |
| 2004/0057802 A1* | 3/2004 | Flolo | B23C 5/1036 407/53 |
| 2006/0015110 A1* | 1/2006 | Pepper | A61B 17/164 606/80 |
| 2009/0048602 A1* | 2/2009 | O'Donoghue | A61B 17/1615 606/80 |
| 2012/0009543 A1* | 1/2012 | Meier | A61B 17/1615 433/165 |
| 2012/0195701 A1* | 8/2012 | Pan | B23C 5/10 407/54 |

* cited by examiner

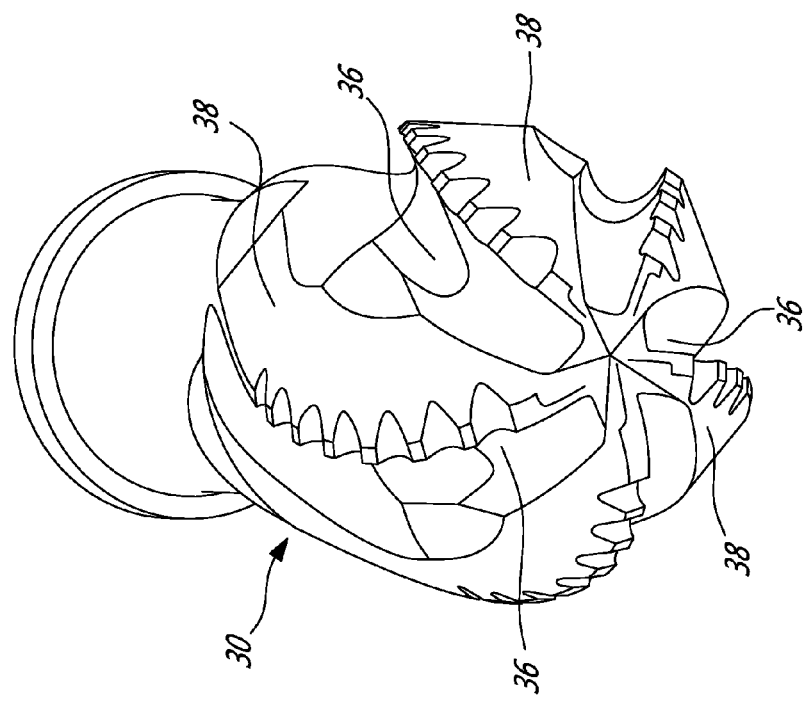
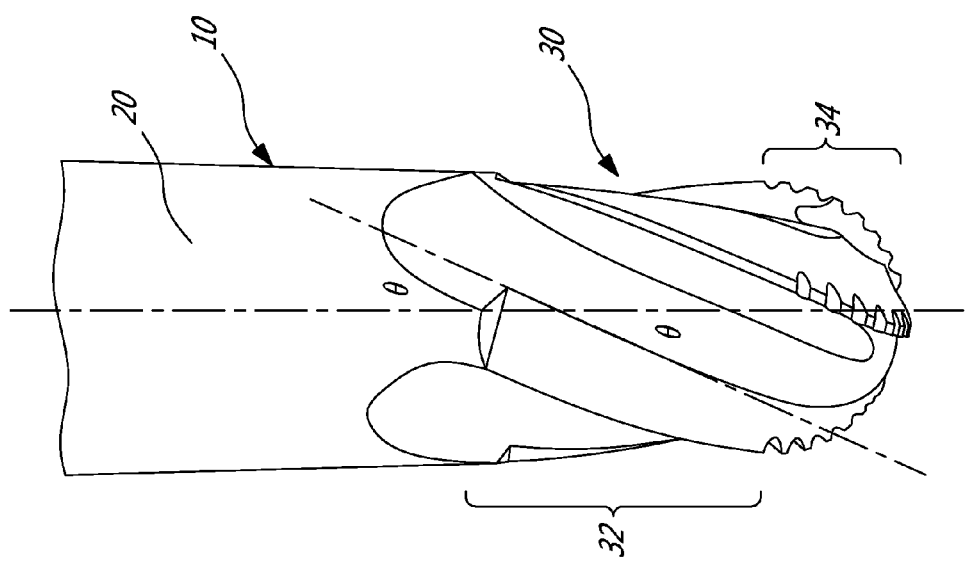

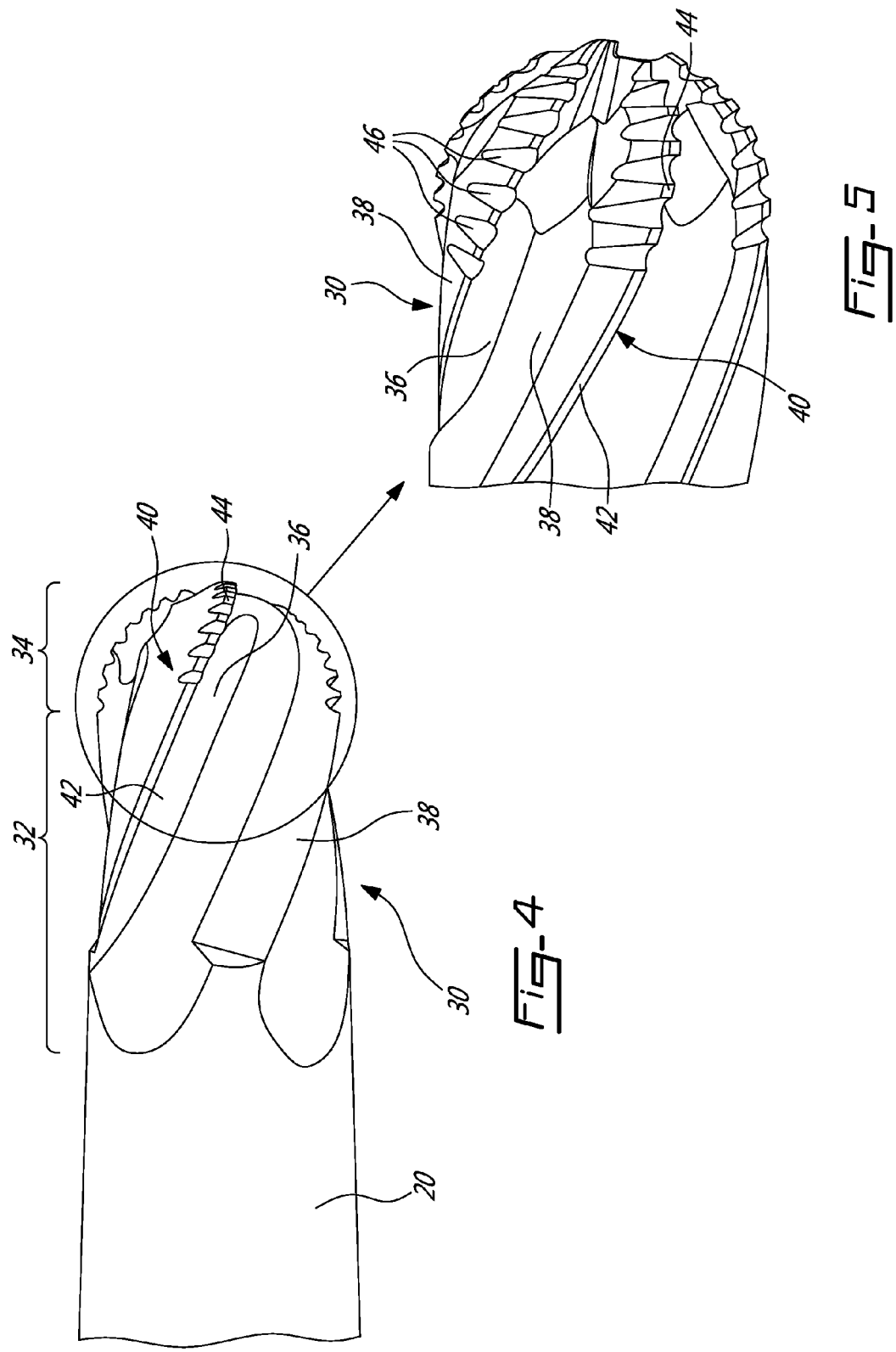

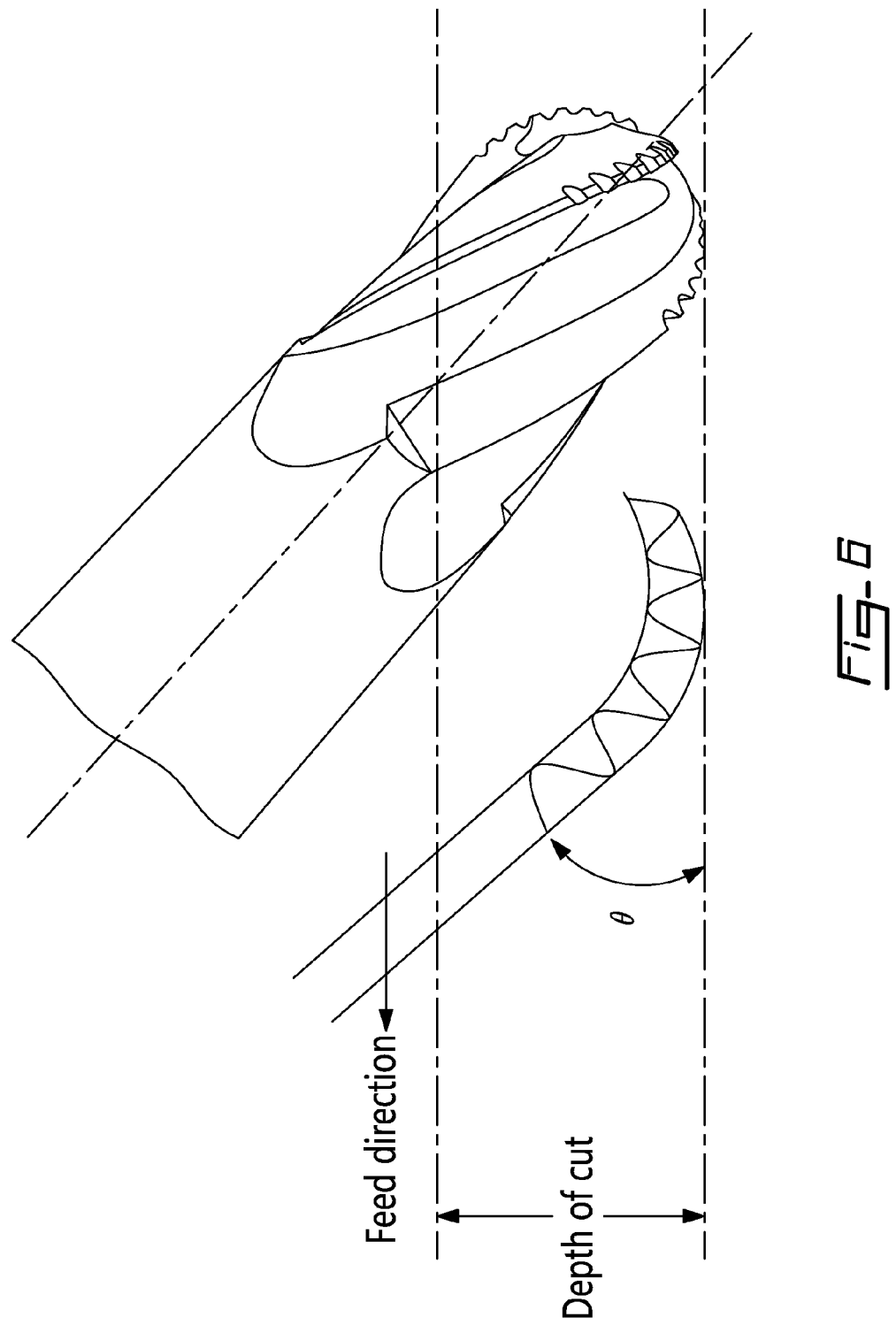

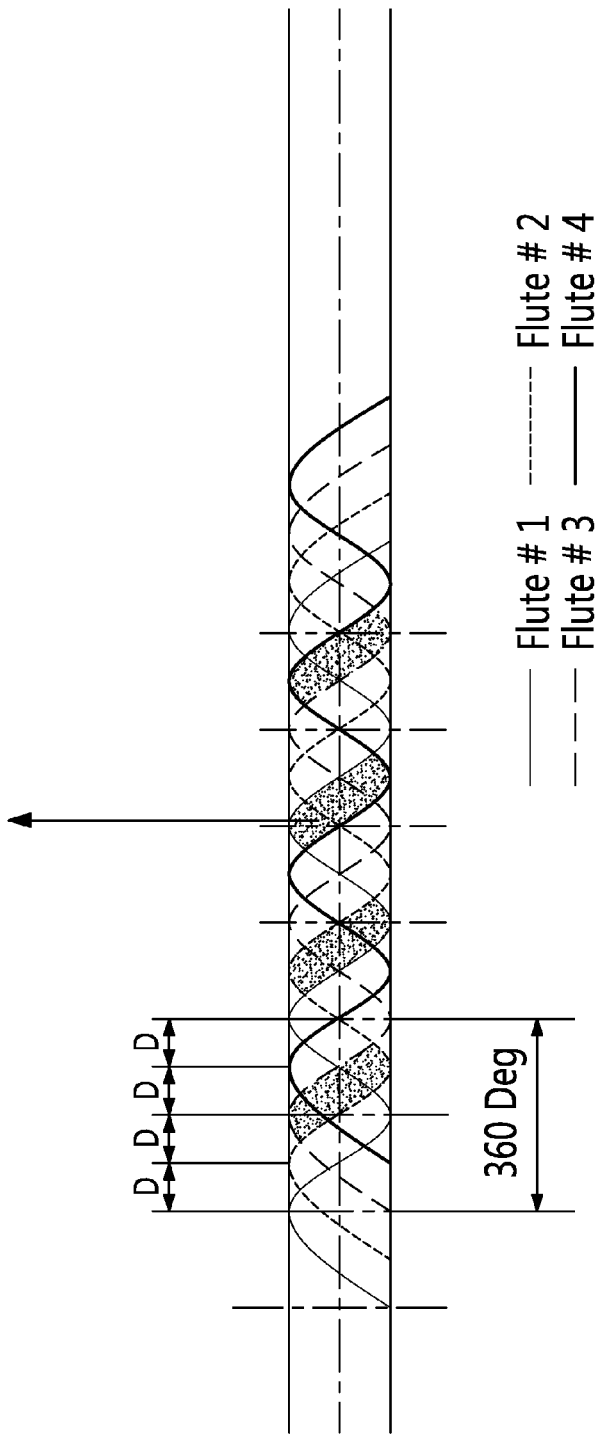

CUTTING TOOL AND CORRESPONDING ASSEMBLY

TECHNICAL FIELD

The present application relates generally to material removal operations, and more specifically to a cutting tool and a corresponding assembly of machining.

BACKGROUND ART

When a long milling tool engages with a workplace only on the tip, the tool tends to vibrate more due to lack of process damping compared to larger engagements. In such cases, time consuming fine tuning is required in the process to avoid chatter vibrations and poor finishing. Most of the time, this leads to longer machining cycle times. Moreover, additional post-machining processes may need to be used to improve the surface finish quality of the workplace. However, these processes may cause dimensional variations on the workpiece and increase the manufacturing cost

SUMMARY

According to an aspect, there is provided a one-piece cutting tool, comprising: an elongated shank portion extending axially between a mounting end and an opposed cutting end, the cutting end having a body portion extending along a body length and terminating in a substantially hemispherical portion, a plurality of flutes defined in the body portion, each flute helically extending adjacent to another flute about the cutting end along a length from the body portion to the hemispherical portion, each flute having a cutting edge divided into a first cutting edge section and a second cutting edge section, the first cutting edge section extending along the body portion and being substantially straight-edged or serrated, and the second cutting edge section extending along the hemispherical portion and being serrated along at least a part of the hemispherical portion.

According to another aspect, there is provided a cutting tool assembly, comprising: a rotatable tool holder; and a one-piece cutting tool, comprising an elongated shank portion comprising a mounting end mountable to the tool holder and an opposed cutting end, the cutting end comprising a body portion extending along a body length and terminating in a substantially hemispherical portion, the cutting end further comprising a plurality of flutes being integral therewith, each flute helically extending adjacent to another flute about the cutting end along a length from the body portion to the hemispherical portion, each flute comprising a cutting edge divided into a first cutting edge section and a second cutting edge section, the first cutting edge section extending along the body portion and being substantially straight-edged or serrated, and the second cutting edge section extending along the hemispherical portion and being serrated along at least a part of the hemispherical portion.

BRIEF DESCRIPTION OF THE DRAWINGS

FIG. 2 is a front view of a cutting tool, according to an embodiment;

FIG. 3 is an end view of the cutting tool of FIG. 2;

FIG. 4 is a side elevation view of the cutting tool of FIG. 2;

FIG. 5 is a magnified view of a cutting end of the cutting tool of FIG. 4;

FIG. 6 is a schematic showing a cutting profile created by the cutting tool of FIG. 2; and FIG. 7 is a schematic showing the amount of material removed by a cutting tool such as the one shown in FIG. 2.

DETAILED DESCRIPTION

Figure 1:
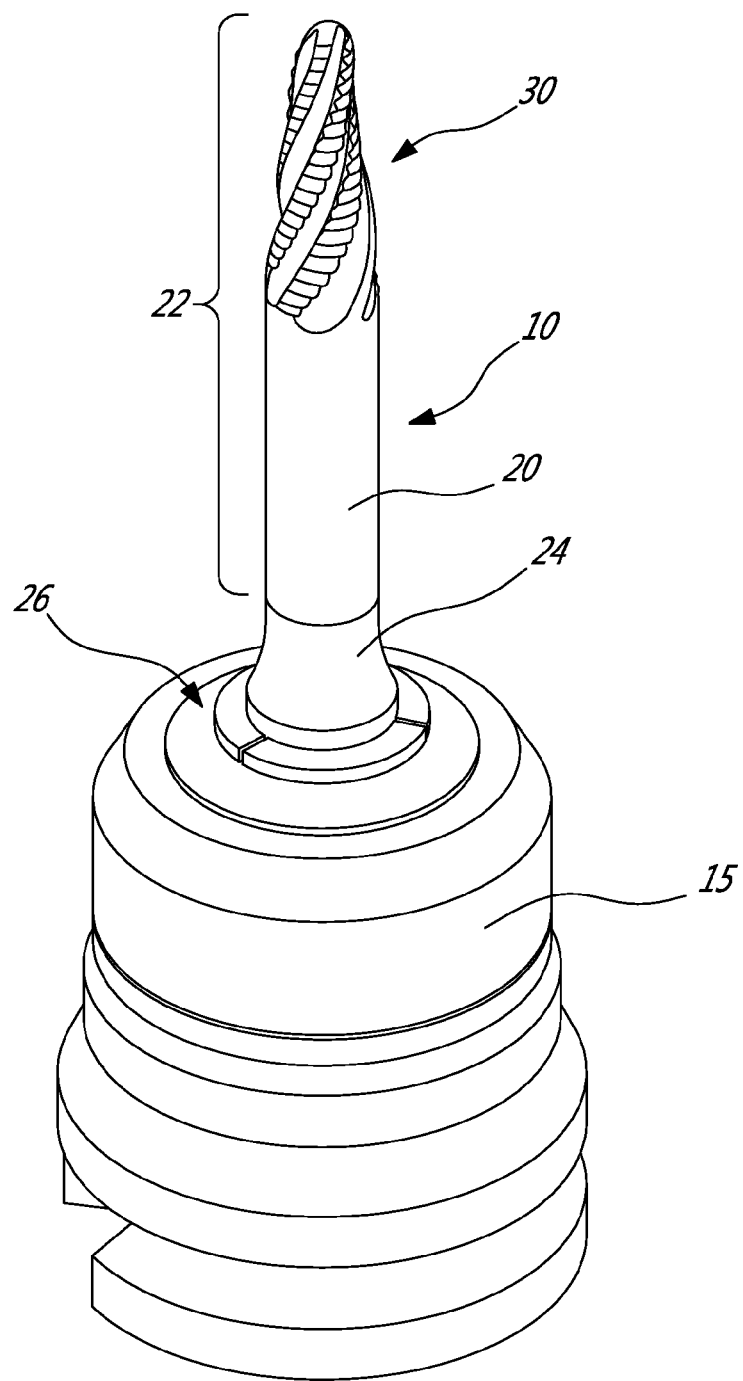
FIG. 1 is a perspective view of a cutting tool assembly.

FIG. 1 shows an embodiment of a one-piece cutting tool 10 mounted to a tool holder 15. The tool holder 15 can be any device to which the cutting tool 10 can be secured so as to be rotated in order to complete its machining operations. The cutting tool 10 (or simply "tool 10") can be any device or object used for machining operations such as cutting, milling, roughing, or finishing against work surfaces or workplaces. In most embodiments, but not necessarily all, the tool 10 is substantially cylindrical in shape. The tool 10 is typically used for end milling operations, but it is not limited to such use. It can be made from a solid carbide. As will become more apparent below, the cutting tool 10 can thus be a one-piece solid carbide helical serrated ball end mill.

The tool 10 has a shank portion 20. The shank portion 20 forms the corpus of the tool 10, and provides structure thereto. It typically is the cylindrical, elongated extension of the tool 10. The shank portion 20 can have a relatively straight back section 24 of the tool 10 that is clamped to the holder of the tool 10.

The shank portion 20 can have a mounting end 26 and an opposed cutting end 30. The mounting end 26 can be mounted to, and removed from, the tool holder 15, which can be a cutting machine, such as a milling machine. The diameter of the mounting end 26 of the shank portion 20, and thus the diameter of the tool 10, may be different from the diameter of the cutting end 30 of the tool 10 discussed below, so that it can be held by a standard tool holder 15. The length of the shank portion 20 can vary depending on the application for which the tool 10 is used, and the clearance required. Other possible factors which can influence the length of the shank portion 20 include its structural configuration, the axial strokes of the machine used to rotate the tool 10, and the size of its spindle. The length allows the tool 10 to be a relatively long, one-piece tool 10 which is suitable for machining difficult to reach places, such as some sections of an airfoil of a compressor.

In some embodiments, the shank portion can have a tapered section 22. The tapered section 22 narrows in the direction of the cutting end 30, and can extend along any length of the shank portion 20. The tapered section 22 forms a taper angle with a central axis of the tool 10. In some embodiments, the length of the tapered section 22 depends on the taper angle and the diameter of the shank portion 20, among other possible factors. The tapered section 22 can extend throughout the length of the entire shank portion 22, or can be ground short as shown in FIG. 1. The taper angle can vary based on numerous factors, such as the diameter of the shank portion 20. Such a taper can advantageously allow the tool 10 to be used for machining operations such as roughing and finishing, on both the side and bottom surfaces of the work piece being machined. However, it is understood that according to some applications, the taper angle can be even zero, thereby providing for straight serrated ball end-mills Referring to FIGS. 2 and 3, the cutting end 30 forms one extremity of the tool 10, and corresponds to the part of the tool 10 that effects the cutting or machining operations.

Referring to FIG. 2, the cutting end 30 has a body portion 32 and a substantially hemispherical portion 34. The body portion 32 extends along a varying body length until it reaches the hemispherical portion 34. The hemispherical portion 34 is shaped similarly to half of a sphere. It forms the rounded tip of the tool 10, such that the tool 10 can be considered a one-piece "ball" end mill. The diameter of the hemispherical portion 34, and thus its size, can vary as required. Although they are described above separately, it will be appreciated that the body portion 32 and the hemispherical portion 34 are integral with one another, thus forming a solid, one-piece tool 10. In contrast, some conventional inserted ball end mills are not one-piece tools because their inserts are attached with a clamping mechanism.

Referring to FIG. 3, the cutting end 30 also has multiple flutes 36 which are of a uniform construction, or integral with, the body of the cutting end 30. The flutes 38 are grooves extending along all or some of the length of the cutting end 30 which allow for the evacuation of machined material away from the cutting end 30 when the tool 10 is in operation. The edges of the flutes 36, or their teeth 38, are protrusions or ridges projecting from the body of the tool 10 and extending along a length. The number of flutes 36 on a given cutting end 30 can vary depending on numerous factors such as, but not limited to: the diameter of the tool 10, the radius of the hemispherical portion 34, and the taper angle. The number of flutes 36 provided on the cutting end 30 can be relatively large, thereby improving finishing. In contrast, conventional inserted or non-one-piece end mills typically cannot have a large number of flutes due to the limitations in locating the inserts around the ball of the tool.

Each flute 36 helically extends adjacent to another, adjacent flute 36. The term "helically" refers to the winding path of each flute 36, in that they wind about the body of the cutting end 30 so as to form a helical pattern, as exemplified in the figures. The tool 10 can thus be considered a helical cutting tool 10.

The expression "extend adjacent" to one another refers to the complementarily of the flutes 36, in that the groove and tooth 38 of each flute 36 is located next to the groove and tooth 38 of an adjacent flute 36. The flutes 38 extend along a length from the body portion 32 to the hemispherical portion 34. In most embodiments, the flutes 36 extend along the entire length, from the beginning of the body portion 32 to the end of the hemispherical portion 34.

Referring now to FIGS. 4 and 5, each flute 36 has a cutting edge 40, which can extend along its tooth 38. The cutting edge 40 corresponds to the part of each flute 36 which engages the surface or piece to be machined. The cutting edge 40 for each flute 36 is divided into a first cutting edge section 42 and a second cutting edge section 44.

The first cutting edge section 42 extends along the body portion 32 and is substantially straight-edged or serrated. The expression "straight-edged" refers to the finish of the first cutting edge section 42 in that it has no serrations, and such a straight-edge can extend along the entire length of the body portion 32. It is typically, but not exclusively, used for finishing-type cuts and machining. In alternative embodiments, the first cutting edge section 42 can be partially serrated if additional roughing is desired. The first cutting edge section 42 follows the helical contour of the flute 36 on which it is located, and typically extends along the length of the flute 36 from the beginning of the body portion 32 to its intersection with the hemispherical portion 34. In most embodiments, the degree of curvature of the first cutting edge section 42 is less than that for the second cutting edge section 44.

The second cutting edge section 44 covers the "ball" or hemispherical portion 34 of the tool 10. The second cutting edge section 44 follows the helical contour of the flute 36 on which it is located, and typically extends along the length of the flute 36 from the beginning to the end point or summit of the hemispherical portion 34. The second cutting edge section 44 is serrated along some, or all, of the length of the hemispherical portion 34. The term "serrated" refers to the row of notches 46 and corresponding projections that are located on the second cutting edge section 44 and which make up its serration profile. In most embodiments, the serration of the second cutting edge section 44 extends along the entire length of the hemispherical portion 34.

The serrated second cutting edge section 44 can be used for both roughing and finishing cuts. When used for finishing operations, a lead angle $\Theta$ can be given to the tool 10 to generate finish-quality cut on the section of the cut where the hemispherical portion 34 of the tool 10 engages with the workpiece, as shown in FIG. 6. This lead angle $\Theta$ can be adjusted based on the profile of the surface being machined, and the required tool vectors to finish the surface. The serrated second cutting edge section 44 can generate additional dampening, which may significantly improve the stability of the tool 10 in both roughing and finishing processes. This improvement may be particularly beneficial when relatively long tools 10 are used, or when the depth of cut is less than radius of the hemispherical portion 34.

The combination of the straight-edged/serrated first cutting edge section 42 and the serrated second cutting edge section 44 can result in a dampening of the vibration experienced by the tool 10, particularly for long cutting tools 10. Furthermore, the serration profiles or notches 46 on the "ball" end of the tool 10 can provide for stable cutting for cuts having a depth that is less than the radius of the "ball" or hemispherical portion 34. The second cutting edge section 44 of the hemispherical portion 34 can help to generate additional dampening and avoid vibrations when roughing the surface, even if the tool 10 is long. At the same time, the straight-edged first cutting edge section 42 can allow for improved finishing of the surface. Thus, the straight-edged/serrated first cutting edge section 42 and the serrated second cutting edge section 44 can help to provide roughing and finishing machining while minimizing vibrations, in contrast, some inserted ball end mills can only be used for roughing operations.

Furthermore, the tool 10 disclosed herein can facilitate cutting to relatively large depths extending from the mounting end 26 to the tip of the cutting end 30. In contrast, the depth of the cut of conventional inserted ball end mills often cannot exceed the radius of the ball.

The angular orientation of the notches 46 can vary from flute 36 to flute 36. Typically, the orientation of the notches follows a sinusoidal pattern being perpendicular to the helical cutting edge 40. The orientation of the notches 46, or their serration profile, on a given flute 36 may be offset or phase shifted from the serration profile of an adjacent flute 36. This phase shift among the serration profiles from flute 36 to flute 36 can be equal to about 360°/N, where N is the number of flutes 36. This angular offset or phase shift of the serration profile of adjacent rows of flutes 36 can advantageously allow for a more efficient removal of machined material from the cutting end 30.

The phase shift between serration profiles can help each flute 36 remove a piece of material in each revolution. This effect can be better appreciated by referring to FIG. 7. The shaded portion schematically represents the amount of material the serration of a given flute 36 can remove from a work surface or piece in each revolution of the tool 10. The serration of each flute 36 helps to remove a relatively small piece of material that was left by the serration of the previous flute 36. The phase shifting can thus improve the stability of the cutting process because the actual depth of the cut is approximately N (being the number of flutes) times less when compared to the engagement of a straight-edge cutting tool.

The embodiments described above are intended to be exemplary. Those skilled in the art will therefore appreciate that the foregoing description is illustrative only, and that various alternate configurations and modifications can be devised without departing from the spirit of the present disclosure. Accordingly, the present invention is intended to embrace all such alternate configurations, modifications and variances which fall within the scope of the appended claims.

The invention claimed is:

1. A one-piece cutting tool, comprising: an elongated shank portion extending axially between a mounting end and an opposed cutting end, the cutting end having a body portion extending along a body length and terminating in a substantially hemispherical portion, a plurality of flutes each helically extending adjacent to another flute about the cutting end along a length from the body portion to the hemispherical portion, each flute having a cutting edge divided into a first cutting edge section and a second cutting edge section, the first cutting edge section extending along the body portion and being substantially straight-edged, and the second cutting edge section extending along the hemispherical portion and being serrated along at least a part of the hemispherical portion with alternating notches and projections to form a serration profile, each projection having a projection height defined from a base of the projection to a tip of the projection, a projection axis being defined for each projection along the projection height, the projection axes of the projections of one of the flutes being phase shifted from the projection axes of the projections of an adjacent one of the flutes by 360°/N, where N is the number of flutes.

2. A one-piece cutting tool as defined in claim 1, wherein the second cutting edge section of each flute has a curvature greater than a curvature of the first cutting edge section of said flute.

3. A one-piece cutting tool as defined in claim 1, wherein the second cutting edge sections of the flutes are serrated along the entire length of the hemispherical portion.

4. A one-piece cutting tool as defined in claim 1, wherein the shank portion comprises a tapered section forming a taper angle with an axis of the cutting tool.

5. A one-piece cutting tool as defined in claim 4, wherein the tapered section extends along the entire length of the shank portion.

6. A one-piece cutting tool as defined in claim 4, wherein the tapered section extends along a part of the length of the shank portion.

7. A one-piece cutting tool as defined in claim 1, wherein the mounting end is removably mountable to a rotatable tool holder.

8. A one-piece cutting tool as defined in claim 1, the cutting tool being a one-piece solid carbide helical serrated ball end mill.

9. A one-piece cutting tool as defined in claim 1, wherein the hemispherical portion defines a ball end such that the cutting tool is a one-piece serrated ball end mill.

10. A cutting tool assembly, comprising:
a rotatable tool holder; and
a one-piece cutting tool, comprising an elongated shank portion extending between a mounting end mountable to the tool holder and an opposed cutting end, the cutting end comprising a body portion extending along a body length and terminating in a substantially hemispherical portion, the cutting end further comprising a plurality of flutes being integral therewith, each flute helically extending adjacent to another flute about the cutting end along a length from the body portion to the hemispherical portion, each flute comprising a cutting edge divided into a first cutting edge section and a second cutting edge section, the first cutting edge section extending along the body portion and being substantially straight-edged, and the second cutting edge section extending along the hemispherical portion and being serrated along at least a part of the hemispherical portion with alternating notches and projections to form a serration profile, each projection having a projection height defined from a base of the projection to a tip of the projection, a projection axis being defined for each projection along the projection height, the projection axes of the projections of one of the flutes being phase shifted from the projection axes of the projections of an adjacent one of the flutes by 360°/N, where N is the number of flutes.

11. A cutting tool assembly as defined in claim 10, wherein the second cutting edge section of each flute has a curvature greater than a curvature of the first cutting edge section of said flute.

12. A cutting tool assembly as defined in claim 10, wherein the second cutting edge sections of the flutes are serrated along the entire length of the hemispherical portion.

13. A cutting tool assembly as defined in claim 10, wherein the shank portion comprises a tapered section forming a taper angle with an axis of the cutting tool assembly.

14. A cutting tool assembly as defined in claim 13, wherein the tapered section extends along the entire length of the shank portion.

15. A cutting tool assembly as defined in claim 13, wherein the tapered section extends along a part of the length of the shank portion.

16. A cutting tool assembly as defined in claim 10, the cutting tool being a one-piece solid carbide helical serrated ball end mill.

* * * * *